US00PP13834P29

(12) United States Plant Patent
Watanabe et al.

(10) Patent No.: US PP13,834 P2
(45) Date of Patent: May 20, 2003

(54) PETUNIA PLANT NAMED 'KIRIMAJI DOUBLE ROSE'

(75) Inventors: Saori Watanabe, Ujiie-machi (JP); Daigaku Takeshita, Utsunomiya (JP)

(73) Assignee: Kirin Brewing Company, Ltd., Tokyo (JP)

( * ) Notice: Subject to any disclaimer, the term of this patent is extended or adjusted under 35 U.S.C. 154(b) by 0 days.

(21) Appl. No.: 10/094,325

(22) Filed: Mar. 8, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Kirimaji Double Rose', characterized by its cascading and prostrate plant habit; freely branching growth habit; early flowering habit; red purple-colored semi-double flowers with brighter red purple-colored venation; and good weather tolerance.

2 Drawing Sheets

BOTANICAL CLASSIFICATION/CULTIVAR DESIGNATION

*Petunia hybrida* cultivar Kirimaji Double Rose.

BACKGROUND OF THE INVENTION

The present Invention relates to a new and distinct cultivar of Petunia plant, botanically known as *Petunia hybrida*, and hereinafter referred to by the name 'Kirimaji Double Rose'.

The new Petunia is a product of a planned breeding program conducted by the Inventors in Tochigi, Japan. The objective of the breeding program is to create new double Petunia cultivars that have stronger growth and attractive flower coloration.

The new Petunia originated from a cross-pollination made by the Inventors in March, 1999, in Tochigi, Japan, of an unnamed proprietary Petunia selection, not patented, as the female, or seed, parent with the Petunia cultivar Double Cascade Pink, not patented, as the male, or pollen, parent. The new Petunia was discovered and selected by the Inventors as a single flowering plant within the progeny of the stated cross-pollination grown in a controlled environment in Tochigi, Japan, in July, 2000. The selection of this plant was based on its strong plant growth habit and attractive flower coloration.

Asexual reproduction of the new cultivar by terminal cuttings taken in a controlled environment in Tochigi, Japan, since July, 2000, has shown that the unique features of this new Petunia are stable and reproduced true to type in successive generations.

SUMMARY OF THE INVENTION

Plants of the cultivar Kirimaji Double Rose have not been observed under all possible environmental conditions. The phenotype may vary somewhat with variations in environment such as temperature and light intensity without, however, any variance in genotype.

The following traits have been repeatedly observed and are determined to be the unique characteristics of 'Kirimaji Double Rose'. These characteristics in combination distinguish 'Kirimaji Double Rose' as a new and distinct cultivar of Petunia:

1. Cascading and prostrate plant habit.
2. Freely branching growth habit.
3. Early flowering habit.
4. Red purple-colored semi-double flowers with brighter red purple-colored venation.
5. Good weather tolerance; tolerant to wind, rain, and low and high temperatures.

Plants of the new Petunia can be compared to plants of the female parent, an unnamed proprietary Petunia selection. In side-by-side comparisons conducted by the Inventors in Tochigi, Japan, plants of the new Petunia differed from plants of the female parent primarily in flower form and color as plants of the female parent had white-colored single flowers.

Plants of the new Petunia can be compared to plants of the male parent, the cultivar Double Cascade Pink. In side-by-side comparisons conducted by the Inventors in Tochigi, Japan, plants of the new Petunia differed from plants of the cultivar Double Cascade Pink in the following characteristics:

1. Plants of the new Petunia were more prostrate and not as upright as plants of the cultivar Double Cascade Pink.
2. Plants of the new Petunia had slightly smaller flowers than plants of the cultivar Double Cascade Pink.

Plants of the new cultivar can be compared to plants of the cultivar Doubloon Pink Star, not patented. In side-by-side comparisons conducted by the Inventors in Tochigi, Japan, plants of the new Petunia differed from plants of the cultivar Doubloon Pink Star in the following characteristics:

1. Plants of the new Petunia had slightly smaller flowers than plants of the cultivar Doubloon Pink Star.
2. Plants of the new Petunia had red purple-colored flowers with brighter red purple-colored venation whereas plants of the cultivar Doubloon Pink Star had light pink-colored flowers with dark purple-colored venation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Petunia.

The photograph on the first sheet comprises a side perspective view of a typical flowering plant of 'Kirimaji Double Rose'.

The photograph on the second sheet comprises a close-up view of a typical flower of 'Kirimaji Double Rose'.

DETAILED BOTANICAL DESCRIPTION

In the following description, color references are made to The Royal Horticultural Society Colour Chart except where general terms of ordinary dictionary significance are used. Twenty-centimeter containers with three plants per container were used for the aforementioned photographs and the following description. Plants were grown under conditions which closely approximate commercial production conditions during the winter in Santa Paula, Calif. in a polyethylene-covered greenhouse. Plants used for the photographs and the description were about 14 weeks from planting rooted young plants. During the production period, day temperatures averaged 28° C., night temperatures averaged 21° C., and light levels were about 5,000 footcandles.

Botanical classification: *Petunia hybrida* cultivar Kirimaji Double Rose.

Parentage:

*Female, or seed, parent.*—Unnamed proprietary selection of *Petunia hybrida*, not patented.

*Male, or pollen, parent.*—*Petunia hybrida* cultivar Double Cascade Pink, not patented.

Propagation:

*Type cutting.*—Terminal vegetative cuttings.

*Time to initiate roots.*—Summer: About 3 days at 25° C. Winter: About 5 days at 23° C.

*Time to produce a rooted young plant.*—Summer: About 21 days at 25° C. Winter: About 23 days at 25° C.

*Root description.*—Fine, fibrous, and white in color.

*Rooting habit.*—Freely branching; dense.

Plant description:

*Form.*—Annual flowering plant; cascading and prostrate plant habit; low mounded; short internodes, dense and bushy appearance.

*Plant height* (*from soil level to top of plant plane*).—About 15 cm.

*Plant diameter* (*area of spread*).—About 130 cm.

*Growth rate.*—Relatively rapid.

*Branching habit.*—Freely basal branching, about 6 to 8 basal branches per plant; lateral branches develop at potentially every node; pinching is typically not required.

*Lateral branch description.*—Length: About 55 cm. Diameter: About 4 mm. Internode length: About 2 cm. Orientation: Initially upright, then horizontal. Texture: Pubescent; short, fine hairs. Strength: Strong, but flexible. Color: 144A.

*Foliage description.*—Leaves simple, generally symmetrical. Arrangement: Alternate before flowering, then opposite. Length: About 5.5 cm. Width: About 3.5 cm. Shape: Broadly elliptic. Apex: Broadly acute. Base: Acute. Margin: Entire. Texture, upper and lower surfaces: Viscid; slightly pubescent. Venation pattern: Pinnate; arcuate. Color: Young and fully expanded foliage, upper surface: 147A. Young and fully expanded foliage, lower surface: 146A. Venation, upper surface: 146B. Venation, lower surface: 146D. Petiole length: About 7 mm. Petiole diameter: About 2 mm. Petiole color: 146C.

Flower description:

*Flower type and habit.*—Flowers face upright or outward; semi-double flower form; solitary and axillary; salverform. Freely flowering habit, about 30 to 34 flowers and flower buds per lateral stem. Flowers persistent.

*Fragrance.*—Faint, sweet, rose-like, and spicy.

*Natural flowering season.*—Spring until frost in the autumn; flowering continuous during this period.

*Time to flower.*—Early flowering; plants begin flowering about 2 weeks after planting.

*Flower longevity on the plant.*—About 2 weeks.

*Flower size.*—Diameter: About 5.25 cm. Length (height): About 3.8 cm. Tube length: About 2.2 cm. Tube diameter, base: About 4 mm.

*Flower buds* (*showing color*).—Length: About 3 cm. Diameter: About 1.1 cm. Shape: Obovate. Color: 186B.

*Corolla.*—Arrangement/appearance: Outer whorl of about five petals fused at base and surrounding inner whorl of about seven to eight petals. Petal length, outer and inner whorls of petals: About 2.5 cm. Petal width: Outer whorl of petals: About 2.6 cm. Inner whorl of petals: About 1.6 cm. Petal shape: Spatulate to flabellate. Petal apex: Rounded with shallow point. Petal margin: Entire. Petal texture: Smooth, glabrous; velvety. Petal surface: Ruffled. Color: Petal, when opening, upper surface: 67A; venation, 66A. Petal, when opening, lower surface: 70C; venation, 144B. Petal, opened flower, upper surface: 74B; color fading to 74C subsequent development; venation, 66A. Petal, opened flower, lower surface: 70C; venation, 144B. Flower throat (inside): 75C; venation, 182A. Flower tube (outside): 75C; venation, 144B.

*Sepals.*—Arrangement/appearance: Single whorl of five sepals fused at base; star-shaped. Length: About 1 cm. Width: About 2 mm. Shape: Narrowly elliptic. Apex: Rounded. Margin: Entire. Texture, upper and lower surfaces: Slightly coarse; pubescent. Color: Young and fully expanded sepals, upper surface: 147A. Young and fully expanded sepals, lower surface: 147B.

*Peduncles.*—Length: About 2 cm. Width: About 1 mm. Strength: Strong. Angle: About 45° from stem. Texture: Pubescent. Color: 146A.

*Reproductive organs.*—Stamens: Quantity: About ten to twelve per flower. Anther shape: Oval. Anther size: About 1.5 mm by 2 mm. Anther color: 158A. Pollen amount: Scarce. Pollen color: 158B. Pistils: None observed.

*Seed/fruit.*—Seed and fruit production has not been observed.

Disease/pest resistance: Plants of the new Petunia have not been noted to be resistant to pathogens and pests common to Petunia.

Weather/temperature tolerance: Plants of the new Petunia are tolerant to rain and wind and have been observed to tolerate temperatures from 3 to 35° C.

It is claimed:

1. A new and distinct cultivar of Petunia plant named 'Kirimaji Double Rose', as illustrated and described.

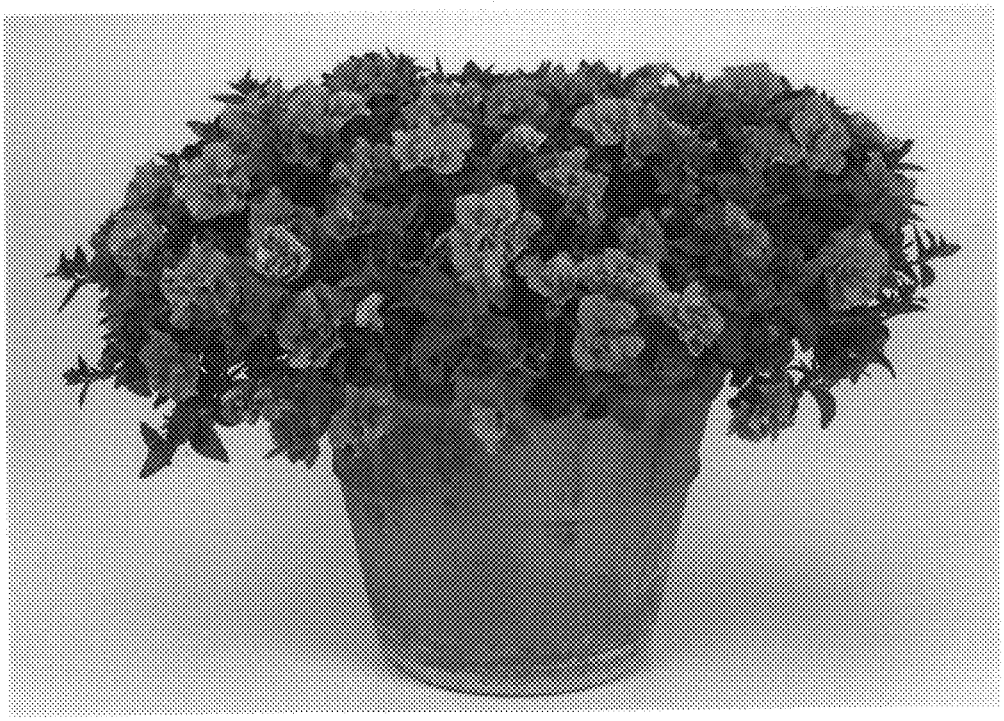

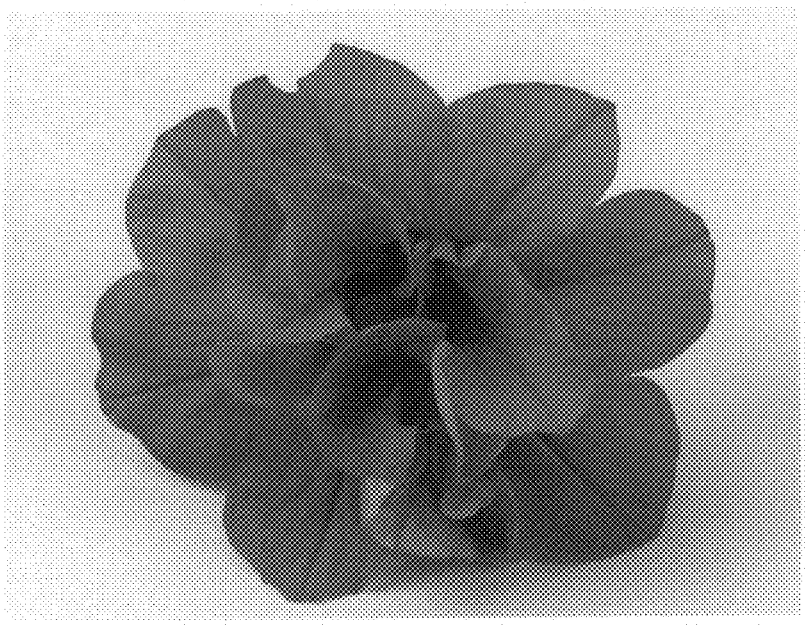

* * * * *